US011234640B2

United States Patent
Rahman et al.

(10) Patent No.: US 11,234,640 B2
(45) Date of Patent: Feb. 1, 2022

(54) NON-INVASIVE PULMONARY FUNCTION ASSESSMENT AND TREATMENT OF RESPIRATORY FATIGUE

(71) Applicant: THE NEMOURS FOUNDATION, Jacksonville, FL (US)

(72) Inventors: Tariq Rahman, Wilmington, DE (US); Thomas H. Shaffer, Chadds Ford, PA (US); Ralph Page, Elkton, MD (US); Jean Remy Bonnefoy, Newark, DE (US); Christopher Page, Newark, DE (US)

(73) Assignee: THE NEMOURS FOUNDATION, Jacksonville, FL (US)

( * ) Notice: Subject to any disclaimer, the term of this patent is extended or adjusted under 35 U.S.C. 154(b) by 313 days.

(21) Appl. No.: 16/020,582

(22) Filed: Jun. 27, 2018

(65) Prior Publication Data

US 2019/0000376 A1 Jan. 3, 2019

Related U.S. Application Data

(60) Provisional application No. 62/525,906, filed on Jun. 28, 2017.

(51) Int. Cl.
*A61B 5/00* (2006.01)
*A61B 5/08* (2006.01)
(Continued)

(52) U.S. Cl.
CPC .......... *A61B 5/4836* (2013.01); *A61B 5/0806* (2013.01); *A61B 5/1135* (2013.01);
(Continued)

(58) Field of Classification Search
CPC ... A61B 5/4836; A61B 5/0806; A61B 5/0809; A61B 5/0803; A61B 5/08; A61B 5/0813;
(Continued)

(56) References Cited

U.S. PATENT DOCUMENTS 4,667,513 A * 5/1987 Konno ................. A61B 5/0488
600/546
5,159,935 A * 11/1992 Sackner ............... A61B 5/1135
600/534
(Continued)

OTHER PUBLICATIONS

R.H. Warren, Chest wall motion in preterm infants using respiratory inductive plethysmography, 1997, ERS Journals, Whole Document (Year: 1997).*
(Continued)

*Primary Examiner* — Joseph D. Boecker
*Assistant Examiner* — Brian T Khong
(74) *Attorney, Agent, or Firm* — Faegre Drinker Biddle & Reath LLP

(57) ABSTRACT

Objective Pulmonary Function (PF) evaluation for respiratory fatigue is vital to the diagnosis and management of many pediatric respiratory diseases in the intensive care, emergency and outpatient settings. A non-invasive PF instrument utilizes sensors and software to access respiratory breathing patterns, vital parameters, asynchrony and measures the work of breathing. Software algorithms predict respiratory fatigue. The hardware includes a microcircuit board that individually links to rib cage (RC) and abdominal (ABD) inductance bands. The bands wirelessly transmit changes in RC and ABD circumference. Point-of-care, real-time indices of respiratory work, breathing patterns and respiratory fatigue indices are developed on a user-friendly graphical user interface. The diagnostic data can later be securely emailed as an attachment for entry into patients' electronic medical records or sent to a caretaker's computer, or used directly to control a respiratory therapy device. The system can also be used for telemedicine homecare.

17 Claims, 9 Drawing Sheets

(51) Int. Cl.
*A61M 16/00* (2006.01)
*A61B 5/113* (2006.01)
*A61B 5/024* (2006.01)
*A61M 16/06* (2006.01)

(52) U.S. Cl.
CPC ...... *A61M 16/0057* (2013.01); *A61M 16/024* (2017.08); *A61B 5/024* (2013.01); *A61B 5/0816* (2013.01); *A61B 5/7225* (2013.01); *A61M 16/0096* (2013.01); *A61M 16/0666* (2013.01); *A61M 2205/3561* (2013.01); *A61M 2205/52* (2013.01); *A61M 2230/40* (2013.01); *A61M 2230/63* (2013.01); *A61M 2230/65* (2013.01)

(58) Field of Classification Search
CPC ..... A61B 5/0816; A61B 5/082; A61B 5/0823; A61B 5/103; A61B 5/085; A61B 5/091; A61B 5/107; A61B 5/1071; A61B 5/1072; A61B 5/1077; A61B 5/1135; A61B 5/113; A61M 16/024; A61M 16/026; A61M 16/022; A61M 2205/52; A61M 2230/40; A61M 2230/42; A61M 2230/63
See application file for complete search history.

(56) References Cited

U.S. PATENT DOCUMENTS

| | | | | | |
|---|---|---|---|---|---|
| 6,015,388 | A * | 1/2000 | Sackner | .................. | A61B 5/411 600/529 |
| 7,827,988 | B2 * | 11/2010 | Matthews | ........... | A61M 16/026 128/204.21 |
| 8,190,249 | B1 * | 5/2012 | Gharieb | ............... | A61B 5/0402 600/508 |
| 8,545,416 | B1 * | 10/2013 | Kayyali | .................. | A61B 5/085 600/534 |
| 2002/0032386 | A1 * | 3/2002 | Sackner | ............... | A61B 5/0022 600/536 |
| 2002/0120207 | A1 * | 8/2002 | Hoffman | ................ | A61B 5/085 600/538 |
| 2003/0139691 | A1 * | 7/2003 | Kumar | .................. | A61B 5/6805 600/587 |
| 2003/0187341 | A1 * | 10/2003 | Sackner | .................. | A61B 5/725 600/388 |
| 2006/0084877 | A1 * | 4/2006 | Ujhazy | ............. | A61M 16/0066 600/483 |
| 2006/0111635 | A1 * | 5/2006 | Todros | ..................... | A61B 5/08 600/484 |
| 2007/0123758 | A1 * | 5/2007 | Miesel | .................. | A61B 5/1116 600/301 |
| 2008/0027341 | A1 * | 1/2008 | Sackner | ............... | A61B 5/0806 600/509 |
| 2009/0020129 | A1 * | 1/2009 | Shaffer | ................ | A61H 31/006 128/845 |
| 2009/0030335 | A1 * | 1/2009 | Kuchler | .............. | A61M 16/021 600/534 |
| 2010/0022904 | A1 * | 1/2010 | Centen | .................. | A61H 31/005 600/534 |
| 2010/0280847 | A1 * | 11/2010 | Schaffer | ................ | G06Q 50/24 705/3 |
| 2011/0257552 | A1 * | 10/2011 | Banet | ..................... | A61B 5/318 600/534 |
| 2012/0065524 | A1 * | 3/2012 | Morren | ................ | A61B 5/1135 600/484 |
| 2014/0123979 | A1 * | 5/2014 | Doyle | ................... | A61M 16/04 128/204.23 |
| 2014/0142652 | A1 * | 5/2014 | Francois | ............ | A61N 1/36034 607/42 |
| 2014/0303503 | A1 * | 10/2014 | Rocque | ............... | A61B 5/0816 600/476 |
| 2015/0254955 | A1 * | 9/2015 | Fields | .................... | G08B 21/02 705/4 |
| 2015/0289785 | A1 * | 10/2015 | Bojovic | ............... | A61B 5/7203 600/534 |
| 2016/0183846 | A1 * | 6/2016 | Derkx | .................. | A61B 5/7264 600/534 |
| 2016/0213286 | A1 * | 7/2016 | Hsiao | ................... | A61B 5/7235 |
| 2016/0270719 | A1 * | 9/2016 | Liu | ...................... | A61B 5/7425 |
| 2016/0287140 | A1 * | 10/2016 | Beyar | ...................... | A61B 5/05 |
| 2017/0285122 | A1 * | 10/2017 | Kaditz | .................. | G01R 33/448 |
| 2018/0113482 | A1 * | 4/2018 | Vitullo | .................. | G06N 20/20 |
| 2018/0220957 | A1 * | 8/2018 | Fuerst | ................. | A61B 5/0022 |

OTHER PUBLICATIONS

Annie Perez, Thoracoabdominal Pattern of Breathing in Neuromuscular Disorders, Aug. 1996, Clinical Investigations, Whole Document (Year: 1996).*
Kathryn Giordano, Pulmonary Function Tests in Emergency Department Pediatric Patients with Acute Wheezing/Asthma Exacerbation, Oct. 2012, Hindawi Publishing Corporation, Whole Document (Year: 2012).*
Fox et al, "Clinical Application of Neonatal Pulmonary Function"; Neonatal Pulmonary Function Testing: Physiological, Technical and Clinical Considerations; 1988, pp. 159-164.
Wright et al., "The Tucson Children's Respiratory Study II: Lower Respiratory Tract Illness in the First Year of LIfe"I; American Journal of Epidemiology, 1989, vol. 129, No. 6, pp. 1232-1246.
Taussig et al., "Introduction", Infant Respiratory Function Testing, 1966, pp. -18.
Warren et al., "Chest Wall Motion in Preterm Infants Using Respiratory Inductive Plethysmography", Eur Respir Journal, 1997, vol. 10, pp. 2295-2300.
Basek et al., "Childhood Asthma and Wheezing Disorders", in Paediatric Pullmonary Function Testing, Progress in Respiratory Research Series, 2005, vol. 33, pp. 204-214.
Jeng et al., "Neonatal Respiratory Care", Hindawi Publishing Corp., International Journal of Pediatrics, vol. 2012, 2 pages.
Giordano et al., "Pulmonary Function Tests in Emergency Department Pediatric Patients with Acute Wheezing/Asthma Exacerbation", Hindawi Publishing Corp. Pulmonary Medicine, vol. 2012, 8 pages.
Jacobus, "Noninvasive Monitoring in Neonatal and Pediatric Care", Chapter 11, pp. 137-146.

* cited by examiner

NON-INVASIVE PULMONARY FUNCTION ASSESSMENT AND TREATMENT OF RESPIRATORY FATIGUE

RELATED APPLICATION

This application is related to and claims priority from U.S. Provisional Application No. 62/525,906, filed Jun. 28, 2017, the disclosure of which is incorporated herein by reference in its entirety.

FIELD OF THE INVENTION

The present application relates to the assessment and treatment of respiratory fatigue, especially but not exclusively in pediatric human patients, and especially to the control of apparatus that provides non-invasive support for the patient's own breathing, such as continuous positive airway pressure (CPAP), BiPAP, High-flow, positive end-expiratory pressure (PEEP), high flow nasal cannulae flow (HFNC), conventional mechanical ventilators with PEEP, high frequency ventilators (HFV), and mechanical ventilators.

BACKGROUND

Objective Pulmonary Function (PF) evaluation for respiratory fatigue is vital to the diagnosis and management of many pediatric respiratory diseases in the intensive care, emergency and outpatient settings.

One known system for monitoring a patient's respiration is respiratory inductive plethysmography (RIP). In this system two bands containing electrical coils are placed round the chest and abdomen of the patient. As the patient breathes, the bands expand and contract, changing the electrical inductance of the coils. An electrical sensor excites the coils, measures the inductance, and thereby measures the expansion and contraction of the chest and abdomen.

Calculated variables include labored breathing index (LBI), phase angle $\Phi$ between abdomen (ABD) and rib cage (RC), breaths per minute (BPM) or respiratory rate (RR), and % RC movement. However, there are currently no real-time approaches to providing non-invasive PF information.

Pulmonary complications are the most frequent problem encountered in sick neonatal/pediatric patients. Nearly 40% of infants wheeze in the first 3 years of life, chronic cough occurs in nearly 13% of 2-year-olds, viral acute respiratory illnesses occur in nearly 20% of infants in the first year of life, and a very large portion of all deaths worldwide are due to respiratory disorders. Asthma in childhood is associated with considerable morbidity and reduced quality of life and is a serious health and economic concern. It is the number #1 cause of hospitalizations in children and represents a significant percentage of pediatric emergency department (ED) visits. Asthma management decisions are largely based on exam findings, vital signs, pulse oximetry and the child's and parents' subjective assessments, which often underestimate the severity of the disease. PF testing is a vital tool in the diagnosis and management of these pediatric respiratory diseases. PF tests that have been developed to analyze tidal breathing in patients who are minimally cooperative due to age or the severity of their condition include respiratory inductance plethysmography (RIP) and pneumotachography (PT).

RIP is currently performed using the SomnoStarPT™ system and Respitrace PT™ system (Sensormedics, Yorba Linda, CA) and has evolved little since the work of Allen et al. (reported in Allen JL, Greenspan JS, Deoras KS, Keklikian EN, Wolfson MR, and Shaffer TH, The interaction between chest wall motion and lung mechanics: Comparable results in normal infants and infants with bronchopulmonary dysplasia, Pediatr. Pulmonol. 11:37-43, 1991). It uses an outdated wired system with cart-mounted computer hardware. The software provides limited real-time graphics and data. The inductive signals from bands worn around the rib cage (RC) and the abdomen (ABD) are treated mathematically and the phase angle ($\phi$) is calculated between them. These and other indices express the work of breathing (WOB) parameters. The displayed parameters can be viewed on the monitor; however, meaningful assessment of the study must be done post-hoc, off-line. At present, this off-line analysis is time-consuming, is not user-friendly and is ineffective for making treatment interventions; therefore it is rarely used in the clinic except for research studies.

Based on previous preclinical and clinical studies it has been shown that respiratory muscle fatigue indices such as phase angle can be ameliorated by increasing end distending pressure via continuous positive airway pressure (CPAP), positive end-expiratory pressure (PEEP) or high flow nasal cannulae flow (HFNC) (reported in Locke R., Greenspan J, Shaffer TH, Rubenstein S D, and Wolfson M R, *The effect of nasal CPAP on thoracoabdominal motion in neonates with respiratory insufficiency*, Pediatr. Pulmonol. 11:259-264, 1991; Frizzola M A, Dysart K, Rodriguez E, Zhu Y, Rojas J, Hesek A, Stump A, Shaffer TH, Miller T L., *Physiologic mechanisms of high flow nasal cannula therapy (HFT) with two degrees of leak around nasal prongs*, Pediatr. Pulmonol. 46(1):67-74, 2011; Jassar R K, Vellanki H, Zhu Y, Hesek A, Wang J, Rodriguez M E, Wu J, Shaffer TH, Wolfson M R, *High Flow Nasal Cannula (HFNC) with Heliox Decreases Lung Inflammation In a Newborn Porcine Lung Injury Model*, Journal of Neonatal-Perinatal Medicine, 2015 Dec. 18; 8(4):323-31, doi: 10.3233/NPM-15915039, PMID: 26757007).

Collectively, these studies showed that in animals and humans with respiratory insufficiency, high phase angles (an index of incipient respiratory fatigue), were reduced by increasing CPAP or HFNC flow, both of which increase intrathoracic pressure. The mechanism is related to stabilization of the chest wall such that respiration is more efficient and requires less work. It was also noted that when Heliox was used as a carrier gas, respiratory work was further reduced as compared to Nitrox as a carrier gas.

SUMMARY

In an embodiment, we describe the development and testing of a prototype for a new non-invasive PF instrument that utilizes any of several types of sensors and software to access respiratory breathing patterns, vital parameters, asynchrony and thus measures the work of breathing. Furthermore, based on experimental data and published literature, we developed software algorithms to predict respiratory fatigue. The hardware includes the design and manufacture of a microcircuit board that individually links to rib cage (RC) and abdominal (ABD) elastic bands. The bands wirelessly transmit changes in RC and ABD data to a data processing device, which may be a tablet device such as an iPad® tablet or firmware. The iPad® software application (App) design and the firmware device includes development of point-of-care, real-time indices of respiratory work, breathing patterns and respiratory fatigue indices on a user-friendly graphical user interface (GUI). The diagnostic data can later be securely emailed as an attachment for entry into patients' electronic medical records or sent to a caretaker's computer. In addition to the above-mentioned health care settings, the system can also be used for telemedicine homecare.

In an embodiment, the sensor is an inductance sensor, which may be conventional, but the instrument may instead use other types of sensor, some of them novel, including strain gauges, optical sensors, magnetometers, accelerometers, and proximity sensors.

By utilizing our rapid wireless method (iPad® tablet/firmware device) to assess work of breathing indices, it is now possible to close the treatment loop. Thus, a clinical operator can increase end-distending pressure (as described in the above reported studies) or the entire system can be closed-loop such that the iPad® tablet or firmware can directly control CPAP, PEEP, or HFNC flow directly depending on the degree of disability. Furthermore, this diagnostic device concept can be combined with other forms of respiratory support (conventional mechanical ventilators with PEEP, as well as high frequency ventilators (HFV) with bias flow for increasing end distending pressure) to treat respiratory insufficiency (respiratory muscle fatigue).

The system now proposed comprises hardware modules that link directly to each compartment band (RC & ABD) and an iPad® application (App) or a firmware digital device that computes and displays these important parameters, as well as new parameters, in real-time, right at the point-of-care. The present system can wirelessly receive RC & ABD data from the patient, display relevant data in real-time, and securely transmit reports and graphics to other locations such as electronic medical records (EMR). Based on previous preclinical & clinical studies, when the present method iPad® tablet/firmware device) for assessing work of breathing indices is utilized, it is now possible to close the treatment loop. Thus, a clinical operator can increase end-distending pressure or the entire system can be closed-loop such that the iPad® tablet or firmware can directly control CPAP, PEEP, or HFNC flow directly depending on the degree of disability. Furthermore, this diagnostic device concept can be combined with other forms of respiratory support (conventional mechanical ventilators with PEEP, as well as high frequency ventilators (HFV) with bias flow for increasing end-distending pressure) to treat respiratory insufficiency (respiratory muscle fatigue).

DETAILED DESCRIPTION

Figure 1:
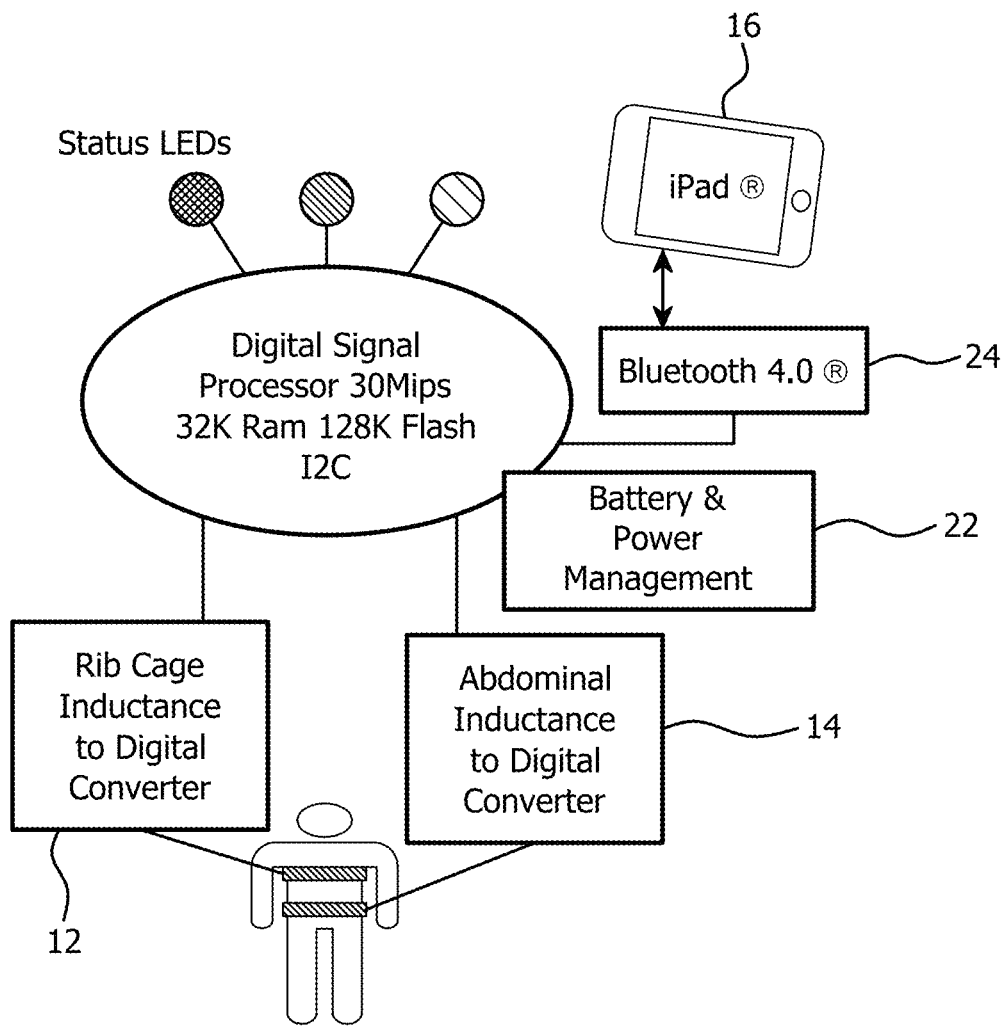
FIG. 1 is a schematic diagram of an apparatus for treatment of respiratory fatigue.

Referring to the drawings, and initially to FIG. 1, one prototype Proof of Concept of Analyzer (referred to as "Design I") is a wireless PF analyzer that uses conventional respiratory impedance plethysmography (RIP) bands to monitor respiratory parameters, FIG. 1 (schematic diagram). This approach offers real-time assessment of work of breathing (WOB) indices and provides secure wireless access via an iPad. Calculated variables include labored breathing index (LBI), phase angle Φ between abdomen (ABD) and rib cage (RC), breaths per minute (BPM), and % RC movement. Results of testing the system with 10 children are presented.

Hardware Design

Figure 2:
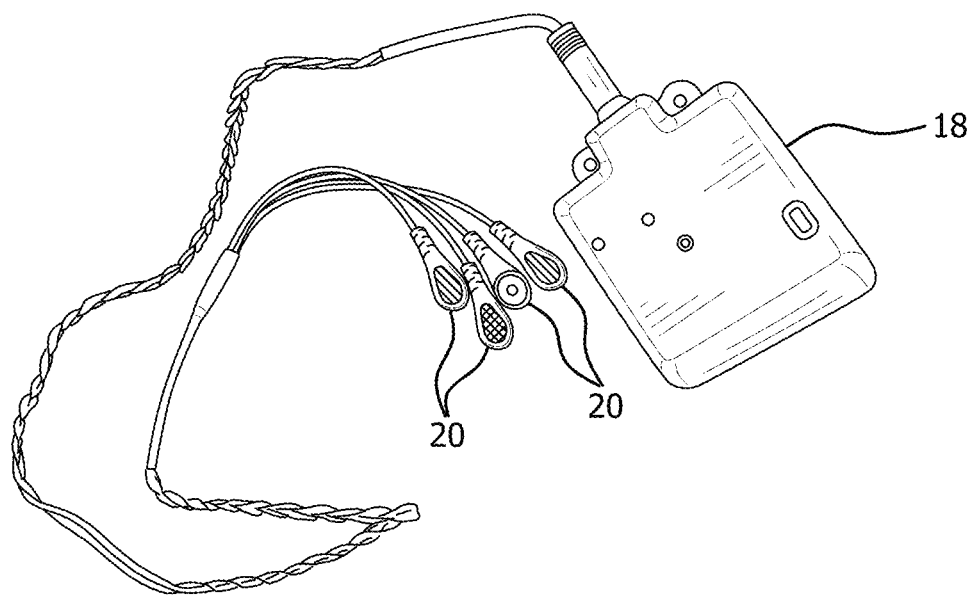
FIG. 2 is a view of a sensor and transmitter module for the apparatus of FIG. 1.
Figure 3:
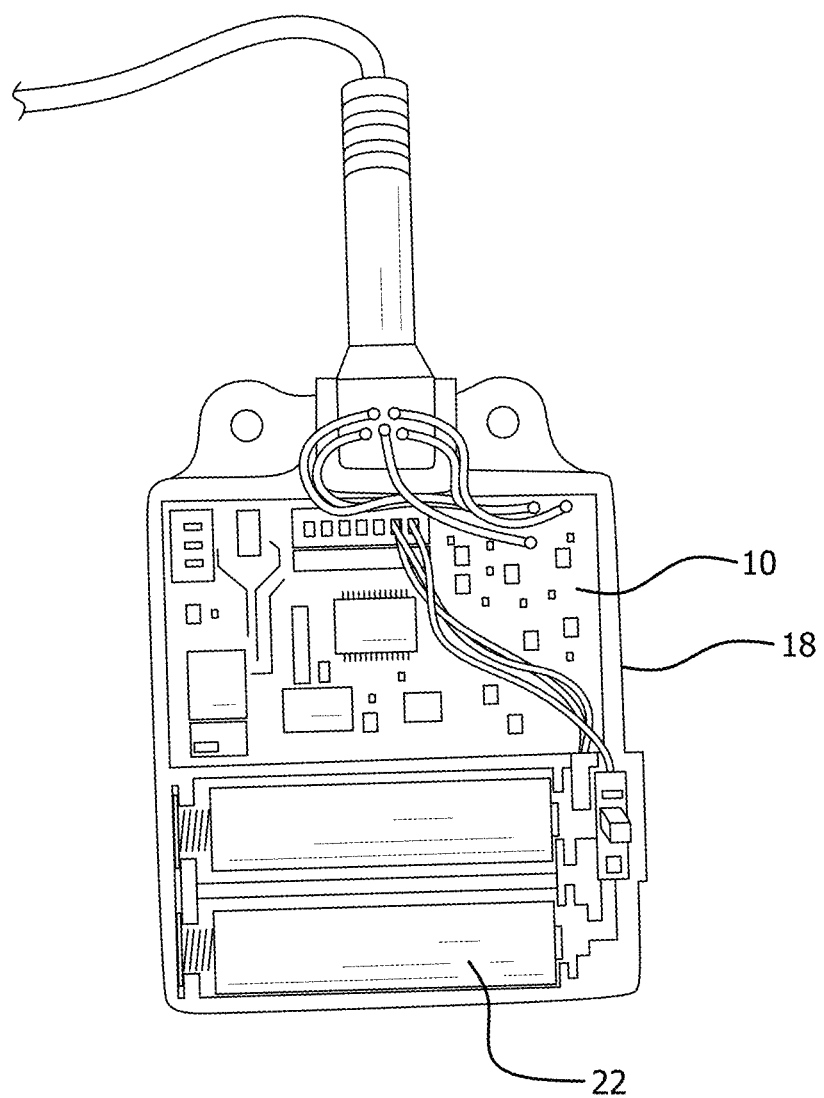
FIG. 3 is an interior view of a module shown in FIG. 2.

Design I includes a single circuit board 10 that incorporates direct digitization of the inductance by a low-energy, high-performance embedded processor. The RC and ABD bands 12, 14 collect data on breathing patterns and forward it to a circuit board 10 that sends the data wirelessly to an iPad® tablet 16. The variables are displayed on the iPad and can be emailed to patient medical records utilizing state of the art secure software. The circuit board, see FIG. 3, is mounted inside a palm-sized plastic enclosure 18 to allow wireless communication while providing protection to the circuitry and the user. The enclosure 18 shown in FIG. 2 is made of lightweight plastic (ABS) and is printed on a Fortus™ 3D printer (Stratasys, Ltd., Eden Prairie, Minn.) 3-D printer. Small polarized connectors 20 that lock are used to connect the inductive bands to the circuit. The enclosure has clear labeling for each connector and light emitting diode (LED) indicators advising use. The unit has a compartment for 2AA batteries 22, accessible to the user for easy battery replacement.

The circuit provides the following functions that provide for a very stable, consistent sensor that does not suffer from measurement drift, and requires no calibration:

Two channels of inductive band inputs connected to the monitor bands 12 14 with locking connectors 20, see FIG. 2.

Two analog acquisition channels, inductive-capacitive (LC) circuit, centered around 250 kHz, and providing an excitation current of a few milli-amps to the bands. The two tuned circuits (one for each band) are carefully separated in frequency to minimize crosstalk. The output from the LC circuit is fed to a low-power Digital Signal Processor (DSP). A self-test circuit, in the form of on-board inductors, provides for reliable and dependable operation.

The DSP implements different algorithms to filter the data, remove unwanted artifacts, further process and package the data and present it to the Radio Frequency (RF) transmitter circuit. The DSP also takes care of power management and sundry control requirements such as on-board LED indicators used for status, Bluetooth connection, battery level and proper connection to the bands.

A non-volatile memory can store measured and pre-processed data, so that once connection is established to the receiving computer, which in the prototype is an iPad® tablet, the pre-connection data is already available and can be immediately transmitted to the iPad® tablet.

An on-board power supply 22, which in the prototype is 2 AA dry cell batteries, powers the circuit 10 and the bands 12, 14, and will last for many hours of continuous use, and many months of 'normal' use. There is no voltage generation above 3 V DC, and no electrical connection to the patient that could inadvertently deliver a higher voltage. Therefore, the device is inherently very safe for the patient electrically.

A short-range wireless interface 24, which in the prototype is Bluetooth® 4.0 (BLE) wireless transmission, provides for very quick connection (pairing) times to the receiving computer of 6 ms or less and uses very low energy for prolonged battery life. It exceeds the bandwidth requirements for real-time data capture and analysis.

Custom embedded software (firmware) programmed into the DSP performs the following operations:

Samples the signals from the inductance bands 12, 14.

Filters the digitized signal using a sequence of finite impulse responses, filtering algorithms, decimated in time to reduce the sampling rate, and to remove extraneous noise.

Encodes the data and packages it, before sending it to the Bluetooth radio transmitter.

Writing software to perform those functions effectively is within the ordinary skill in the art and, in the interests of conciseness, the details are not further described here.

The software stores and keeps samples of the processed readings from the bands available in the non-volatile memory if the Bluetooth has not yet been connected, or in the event of a short transmission interruption, so that, upon connection or re-connection, the stored samples can then be transmitted, ensuring no valuable data are lost. However, because this device is intended for real-time use, as is explained below, typically from 10 to 60 minutes of the most recent data are actually used. There is thus no reason to store older data, and a large non-volatile memory is therefore not required, provided the memory is one that can be continually overwritten and effectively functions as a non-volatile circular buffer.

The firmware also monitors battery and usage, and is responsible for power management.

Software for Analyzer Design

A mobile device application, which in an embodiment is an iOS application (App) or digital firmware is designed to connect to the monitor, download the data, compute, display and share the information. The software continually scans for available transmitting devices within the effective range of the Bluetooth connection (around 100 feet, 30 meters). Because the receiving application is intended to interface only with a small number of known transmitting units, both the transmitter and the receiver can be preconfigured with usernames, passwords, coding schemes, encryption keys, and the like. It is thus easily possible to establish a communication link that is secure against interception, robust against interference, and does not interfere with other transmissions or sensitive devices that may be found in a hospital environment.

A wired connection could be used but, especially in a hospital ICU environment, the number of physical connections to a patient easily becomes so large that the connections interfere with each other, or obstruct the activities of treating personnel. Using a wireless connection is thus preferred.

Once a transmitting device is detected and selected, the user has immediate access to any stored data from the transmitting device, which can be displayed as numbers, graphs, or in any convenient format. Thereafter, the data is updated in real-time. The application also allows for the user to modify the device name, set a location name, store patient data, as well as email all of the data in any desired format, such as EDF+(extended European Data Format), comma separated variables, (CSV), or SQLite as an attachment. Signal processing to compute these parameters uses a combination of data windowing, finite impulse response filtering (FIR), and fast Fourier transforms (FFT). Judicious use of FFT and weighted averaging also provides for improvements in signal-to-noise ratio. In an embodiment, the iPad processing power is utilized to compute the following respiratory indices in real-time:

1. Phase Angle (Φ): The phase angle (Φ) between the rib cage (y) and abdomen (x) values is calculated by normalizing the signals over 20 samples. It is then calculated by the following formula:

$$\phi = \cos^{-1}[\Sigma x(n)y(n)]/(\{\sqrt{\phantom{x}}[\Sigma x(n)^2 \Sigma y(n)^2]\}) \quad (1)$$

where all Σ are sums from n=0 to N−1.

2. Respiratory Rate (Breaths per minute): We use an FFT algorithm to generate the average magnitudes for each frequency of the abdomen and rib cage signal. From these calculations, an array is generated from which the largest value is selected, as well as amplitudes within 20% of this value. Finally, we compute a weighted average using indices of these values. This value is the frequency multiplied by 60 to obtain breaths per minute.

3. Percentage rib cage (% RC): We use an FFT algorithm to generate the magnitudes for each frequency of the abdomen and rib cage signal. From this transformation, an array is generated that has a set of indices. We then select the index with the largest amplitude of both signals. The following formula is used:

$$\% \text{ RC} = [|RC|/(|RC|+|ABD|)] \times 100 \quad (2)$$

4. Labored Breathing Index (LBI): Asynchronous breathing is less efficient than synchronous breathing. LBI is an indication of the additional work of breathing when breathing is asynchronous. This estimation is calculated by summing the phase relationship between ABD and RC values relative to their sum per unit of time [17]. The FFT of the signals generates the phase-magnitude relationship of the ABD and RC signal relative to the sum. From these calculations, an array is generated that has a set of indices from which we select the index with the largest amplitude.

$$LBI = [(P+Q)+(R+S^1)]/[(P+Q)+(R+S)] \quad (3)$$

where P and Q are the trough and peak volumes for the rib cage, R and S are the trough and peak volumes for the abdomen, and S' is the abdomen value at the time of ribcage peak Q. The denominator is the tidal volume.

Figure 4:
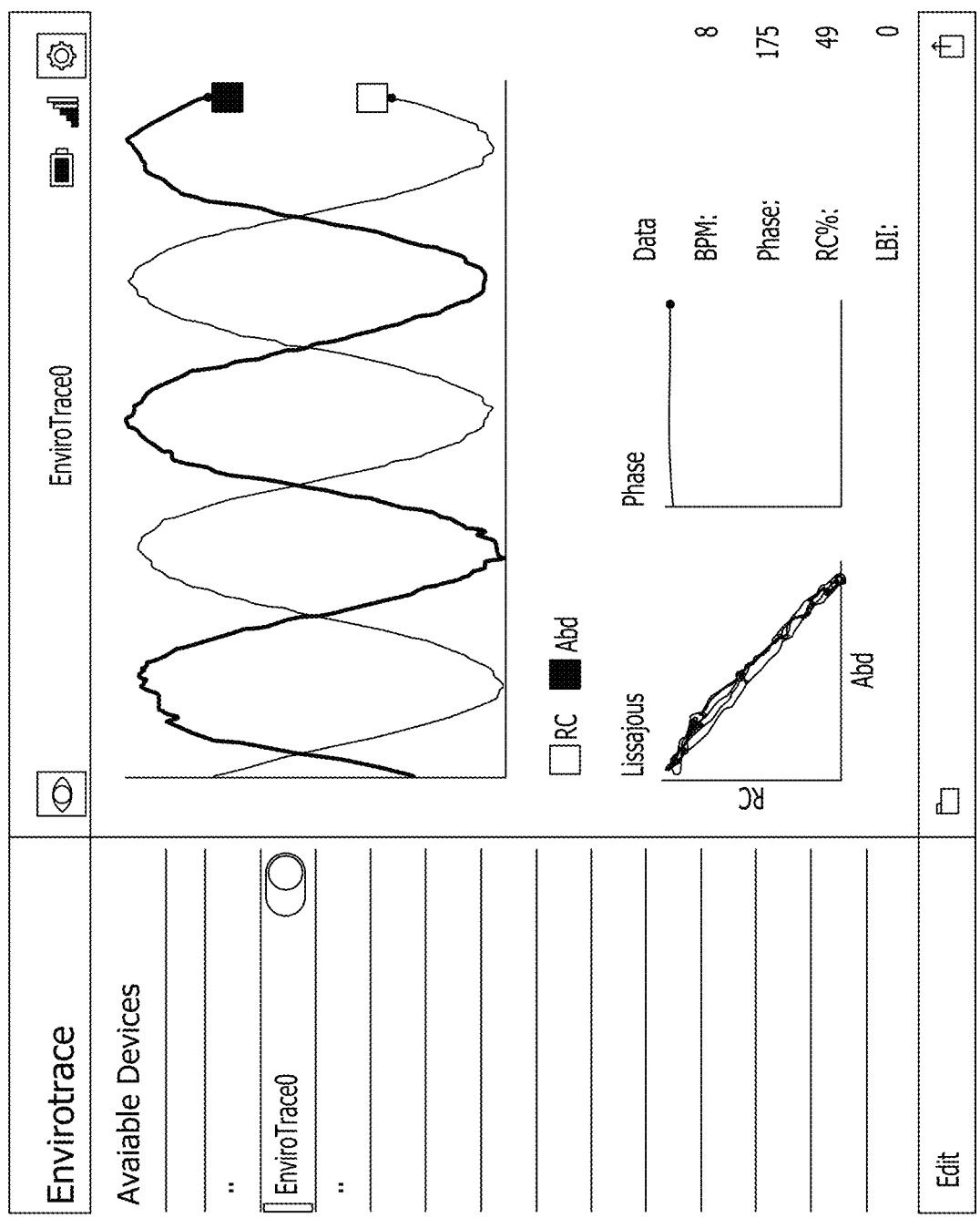
FIG. 4 is an example of a display of data.

Finally, a summarized report for the entire study is provided (FIG. 4). The results shown in the report are based on the mean of selected breaths over 5 to 60 mins (the study period can be varied). Based on clinical experience subjects/patients are typically observed for at least 10 minutes to insure a sufficient number of viable breaths. Unacceptable breaths associated with movement artifact and signal noise are filtered from the report information. In addition, means, % variance, graphics and normative historic data are included in the report for comparison. In a practical implementation, the display could be on the transmitter, though that would limit the amount of information that could be displayed, on the respiratory support device, on a separate computer such as the iPad used in the prototype, or on a separate display unit, which may or may not be shared with other equipment. The use of wireless communication, so that cooperating devices do not have to be physically very close in order to minimize undesirable tangles of cables and tubing, greatly enhances the possible versatility in configuration.

Bench-Top Testing

Figure 5:
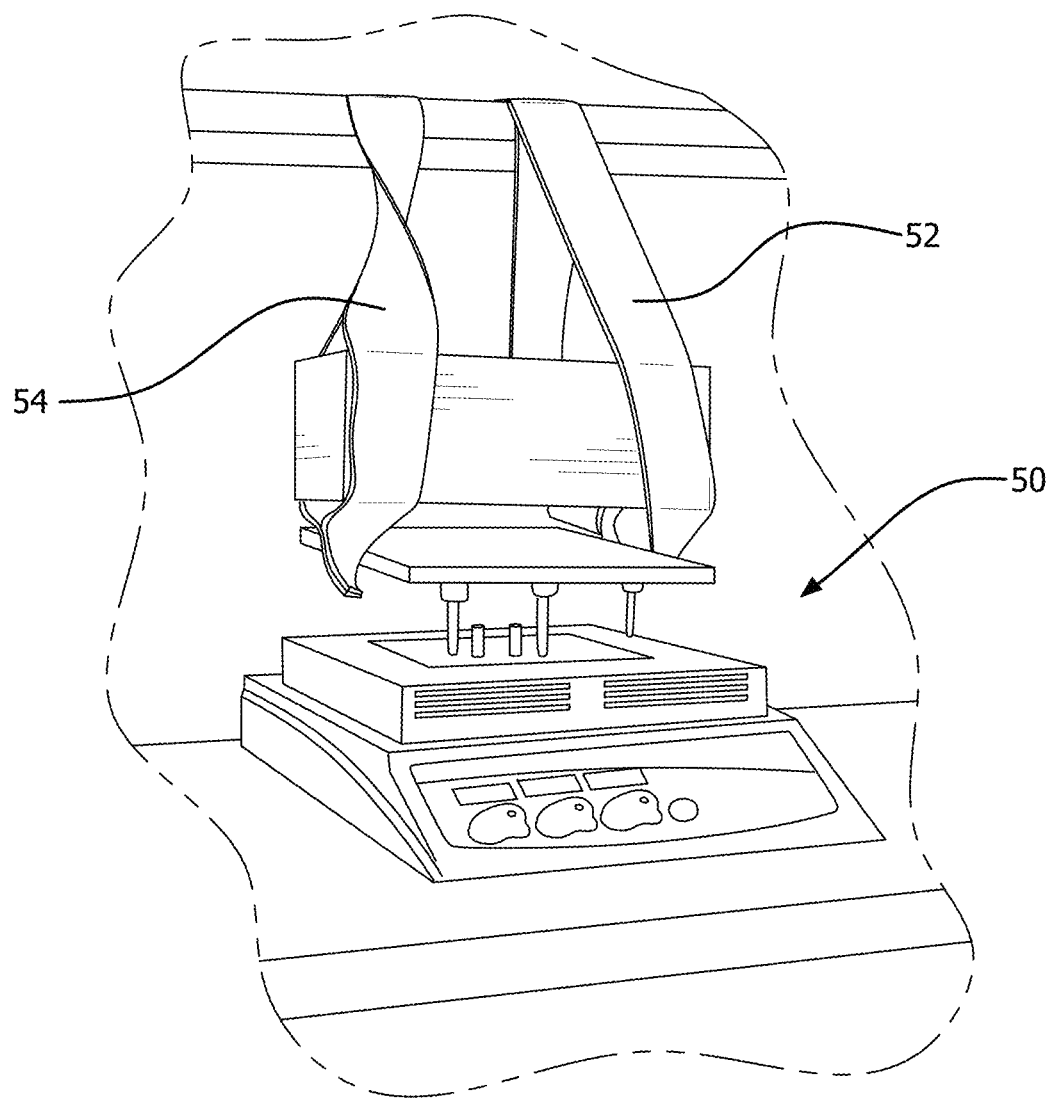
FIG. 5 is a perspective view of an in vitro test setup for the apparatus of FIGS. 1-4.

Bench-top experiments were conducted to determine the reliability, sensitivity, and reproducibility of the circuitry and instrument design. This involved mounting the RIP bands 52, 54 on a laboratory-grade rocker/waver platform 50, as shown in FIG. 5. The tilt angles and speed were varied to simulate different breathing conditions. The test was conducted continuously over two days.

Subject Testing

After Institutional Review Board approval and consent, 10 normal subjects (10-17 yrs) were tested in random order under baseline conditions and with an added resistive load. Testing was conducted to demonstrate: a) that the new system will provide breathing indices as accurately as the existing SomnoStar™ PT system (which is widely considered the "gold standard"); and b) that the new prototype accurately differentiates between breathing under load and no-load breathing conditions. The bands were placed on the subject with the monitor activated and he was asked to breathe normally for 3 minutes. This was repeated while breathing under load. The load was an external bidirectional laminar resistive load (Hans Rudolph, Inc. Shawnee KS) and 20 cm $H_2O$ per liter per second were provided to each subject. This was similar to breathing through a straw. Both conditions were repeated using the SomnoStar™ PT system. The following measures were recorded: average phase angle between RC and ABD, average LBI, average % RC and BPM. The order of testing was randomized.

Although an actual prototype has been described above, various design modifications are possible, and may be desirable, to achieve an optimum design of our noninvasive method for assessment of respiratory function, breathing parameters and prediction of respiratory fatigue for clinical use. For example, instead of respiratory impedance plethysmography (RIP) bands, strain gauge bands or accelerometers may be used on the RC and ABD. For example, each band may have a link that secures the bands around the patient and transmits individual RC and ABD data directly to the iPad® tablet or other wired or wireless receiver, instead of the data being collected and analyzed by the device of FIGS. 2 and 3 attached to the patient, and then transmitted. This design also allows a connection for EKG leads to assess heart rate (HR), which has been shown to become elevated during respiratory loading. This approach also offers real-time assessment of WOB indices and provides secure wireless access via an iPad.

If the local transmitter of FIGS. 2 and 3 is used, then it may also collect and transmit EKG or other monitoring signals, further reducing the number of physical connections to the patient.

Calculated variables include labored breathing index (LBI), phase angle Φ between abdomen (ABD) and rib cage (RC), breaths per minute (BPM) or respiratory rate (RR), and % RC movement. Furthermore, we have reviewed the literature (including our own work) to develop normative values and algorithms for labored breathing index (LBI), phase angle Φ between abdomen (ABD) and rib cage (RC), breaths per minute (BPM) or respiratory rate (RR), % RC movement and HR as a function of age. These normative data allowed us to develop a respiratory fatigue index (RFI), which is a weighted scoring index based on a patient's LBI, Φ, RR, HR and variance in phase angle (σ). This index is a biomarker index that has been investigated to provide an overall estimate of respiratory fatigue. The RFI will be weighted by summing the parameters below:

$$RFI = \alpha_1(\Phi) + \alpha_2(LBI) + \alpha_3(RR) + \alpha_4(HR) + \alpha_5(\sigma) \quad (4)$$

In an embodiment, the calculation may be simplified by expressing the respiratory variables Φ, LBI, RR, HR and σ as numerical scores. For example, they may be scored as follows:

TABLE 1

| Variable | Score 1 | Score 2 | Score 3 | Score 4 |
|---|---|---|---|---|
| Φ | <45 deg | 45-100 deg | 100-180 deg | >180 deg |
| LBI | <1 | 2-3 | 3-4 | >4 |
| RR | <25 | 25-35 | 35-45 | >45 |
| HR | <10% | 10-15% | 15-20% | >20% |
| σ | <10% | 10-30% | 30-50% | >50% |

In Table 1, the HR score is a % variance from the normal values given in Table 2. The RR score is based on the variance from normal at specific ages.

Reducing the RFI to a simple number may reduce precision, but has the advantage of being simple for an attending caregiver to interpret, or for a simple servo-mechanism to respond to.

In actual use, it may not be necessary to use all five variables. In order to simplify computation, only the phase angle Φ and/or the Labored Breathing Index may be used, equivalent to setting one or more of $\alpha_3$, $\alpha_4$, and $\alpha_5$ equal to zero.

Whatever system is used to compute the RFI, a servo control might be pre-programmed with upper and lower bounds for a permissible range, so that the level of intervention is increased or decreased when the RFI moves outside those bounds. Where different ranges are permissible for different categories of patient, for example, neonatal, pediatric, and adult ranges, the correct category may be selected from a list. The physician would have power to override the preset bounds, but that should seldom be necessary. The bounds may be dependent on the age of the patient, which may be entered into the system when it is activated for that patient. For example, typical values of heart rate are as follows:

TABLE 2

HR NORMAL VALUES AS A FUNCTION OF AGE
Normal Heart Rate by Age (Beats/Minute)

| Age | Awake Rate | Sleeping Rate |
|---|---|---|
| Neonate (<28 days) | 100-205 | 90-160 |
| Infant (1 month-1 year) | 100-190 | 90-160 |
| Toddler (1-2 years) | 98-140 | 80-120 |
| Preschool (3-5 years) | 80-120 | 65-100 |
| School-age (6-11 years) | 75-118 | 58-90 |
| Adolescent (12-15 years) | 60-100 | 50-90 |

Thus, higher thoraco-abdominal fatigue is indicated by a high summation RFI. During recent studies we noted that ER patients requiring admission to the hospital and neonatal intensive care unit (NICU) infants tended to exhibit higher than normal (for age) values of these selected physiological parameters.

In an embodiment, when using all coefficients α to determine RFI, initially all of the coefficients will be set to 1.0 before the first therapeutic intervention (for example, change in CPAP level). After the first intervention, the algorithm will then compare respective responses across all parameters to determine how closely each parameter reached its target. On the next calculation of RFI, the coefficients α will be adjusted to normalize the next intervention in order to bring the low responders higher and the high responders lower, thus bring all factors closer to their respective normal range. This numerical process will continue until the patient parameters are within the normal range or until the therapeutic intervention reaches its maximum intervention (for example, infants: max CPAP=12 cm $H_2O$; pediatrics: max CPAP=25 cm $H_2O$; and adults: max CPAP=40 cm $H_2O$).

Thus, these coefficients will provide best-fit analysis for the optimum correction of RFI in the relatively shortest reasonable clinical response time. Note that respiratory scoring of these physiological parameters is age-dependent and will be built into the software (see below). In addition, numerical analysis of tidal flow-volume relationships allowed calculation specific (peak flow/mid-flow) calculations at mid-tidal volume enabling a prediction of obstructive flow problems. The combination of RIP calculations in parallel with flow-volume calculations provides a differentiation between respiratory fatigue mechanisms-restrictive versus obstructive lung problems.

Figure 6:
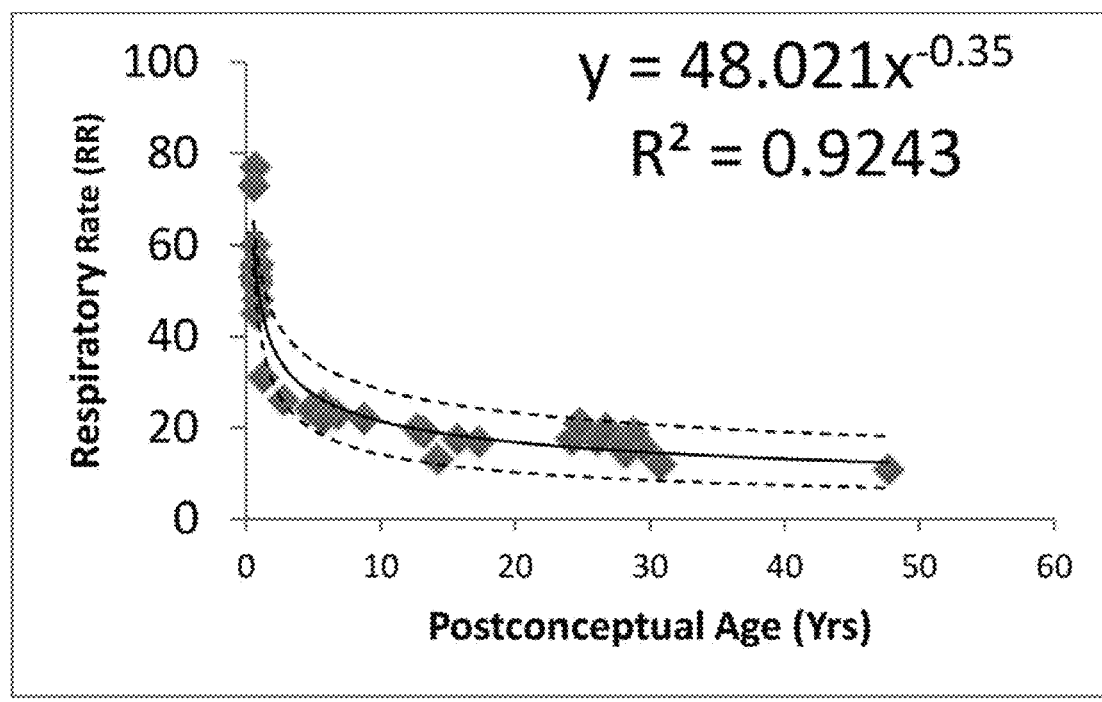
FIGS. 6-8 are graphs.
Figure 7:
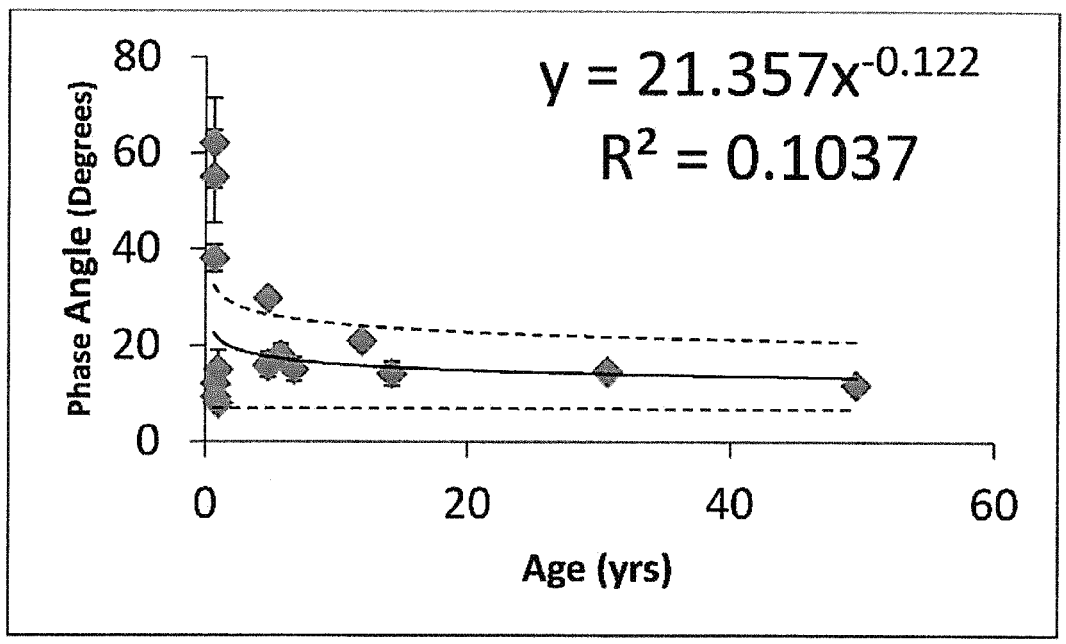
Figure 8:
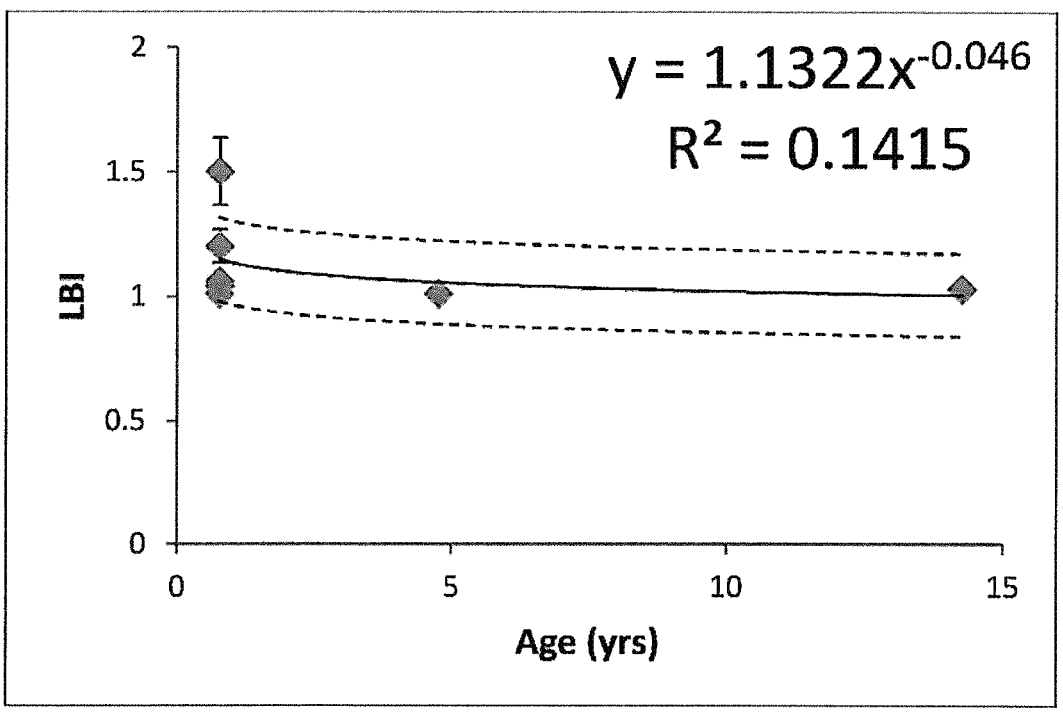

FIGS. 6-8 are graphs illustrating the normative data for each parameter as a function of age. The solid line is the best fit and represented by the equation in each case, not always a linear fit. The dashed lines represent 15% variance from the best fit line & R is the regression coefficient where R=1.0 is a perfect fit.

Analyzer Hardware Design Prototype & Treatment Feedback Loops

Analyzer design II includes two microcircuit boards that incorporate direct digitization of the inductance, strain, or acceleration (integrated for displacement) by a low-energy, high-performance embedded processor. Individual RC and ABD bands collect data on breathing patterns and forward it to a connected microcircuit board that sends the data wirelessly to an iPad, a process similar to prototype II. The variables are displayed on the iPad® tablet and can be emailed to patient medical records utilizing the same state-of-the-art secure software. The microcircuit board is mounted inside a small plastic enclosure (the size of a button, 3 cm dia×1 cm thick) to allow wireless communication while providing protection to the circuitry and the user. The enclosure is made of lightweight plastic (ABS) and is printed on a Fortus™ 3D printer (Stratasys Ltd., Eden Prairie, Minn.) 3-D printing machine. Small link connectors that lock are used to connect each band (RC & ABD) to the circuit. In addition, the RC link connector also has a port for EKG leads to transmit HR to the iPad. Each enclosure has clear labeling (RC & ABD), as well as LED indicators advising use. The unit has a compartment for small lithium batteries, accessible to the user for easy battery replacement.

Open-Loop and Closed-Loop Treatment Options

As previously noted, utilizing the present method (iPad® tablet/firmware device) for assessing work of breathing indices, it is now possible to close the treatment loop. Thus, a clinical operator can increase or decrease end distending pressure or the entire system can be closed-loop such that the iPad® tablet, firmware, or other controlling processor can directly control a CPAP, PEEP, HFNC flow, or other breathing assist device, depending on the degree of disability. Furthermore, this diagnostic device concept can be combined with other forms of respiratory support (conventional mechanical ventilators with PEEP, as well as high frequency ventilators (HFV) with bias flow for increasing end distending pressure) to treat respiratory insufficiency (respiratory muscle fatigue).

As outlined herein, the analyzer senses the respiratory indices from the patient. If these indices are abnormal (normal ranges provided above), input to the patient (CPAP, ventilator, HFV, etc.) is automatically adjusted. This feedback system constantly compares the desired respiratory index, such as phase angle between the abdomen and rib cage, and compares the index to the actual measurement. If there is no difference in the two measurements then the system does not change anything. The respiratory assistance continues at its previous level. If the actual index does not match what is desired, the system automatically adjusts the input in a stepwise fashion until they are aligned. The system may be programmed to make no more than one adjustment in a specified time period, for example, five minutes, in order to allow the patient to respond to the initial adjustment and the requirements to be reassessed before another adjustment is made. The desired indices may cover a range of values that are considered normal for a particular patient. The feedback system as shown in the block diagram in FIG. 9 applies the best feedback gains to bring the actual values (phase angle, LBI, RFI,) within the desired range. The gains are user-selected and initially based on previous studies.

The gains may be proportional (P) and derivative (D) in nature so that action is taken based not only on how far the actual value is from the desired value but also on how fast the actual is approaching the desired value. An integral (I) or adaptive gain component may also be added. This is when the settling time of the signal may be modulated, which controls how fast the signal settles to the desired value. The adaptive gain is based on whether a patient has respiratory muscle fatigue and requires improvement; or is getting worse and requires an accelerated change in gain, or is in the recovery phase and can tolerate more rapid adjustments in pressure/flow control. As shown, the clinical operator can be in the loop and make adjustments to CPAP, HFNC, or vent based on the output. In the closed-loop operation, the operator sets the desired levels required and the system sends signals to servomotors which adjust pressure/flow setting automatically.

Figure 9:
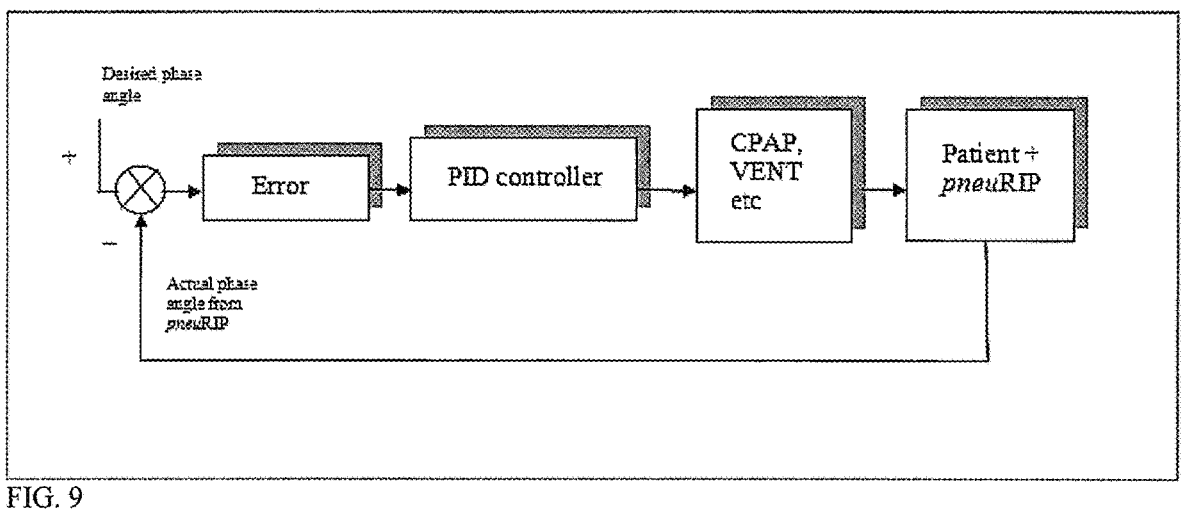
FIG. 9 is a block diagram of a control system including the apparatus of FIGS. 1-4.

FIG. 9 shows a closed-feedback loop for automatically adjusting the respiratory support device to reduce respiratory muscle fatigue: in the presented case, adjustments are based on phase angle whereas adjustments could be based on several factors such as Phase angle, LBI, RFI, etc. In the embodiment, the block "Patient+pneuRIP" may include the preprocessor and transmitter of FIGS. 2 and 3, and the comparator and the blocks "error" and "PID controller" may be the iPad or other controlling processor.

Figure 10:
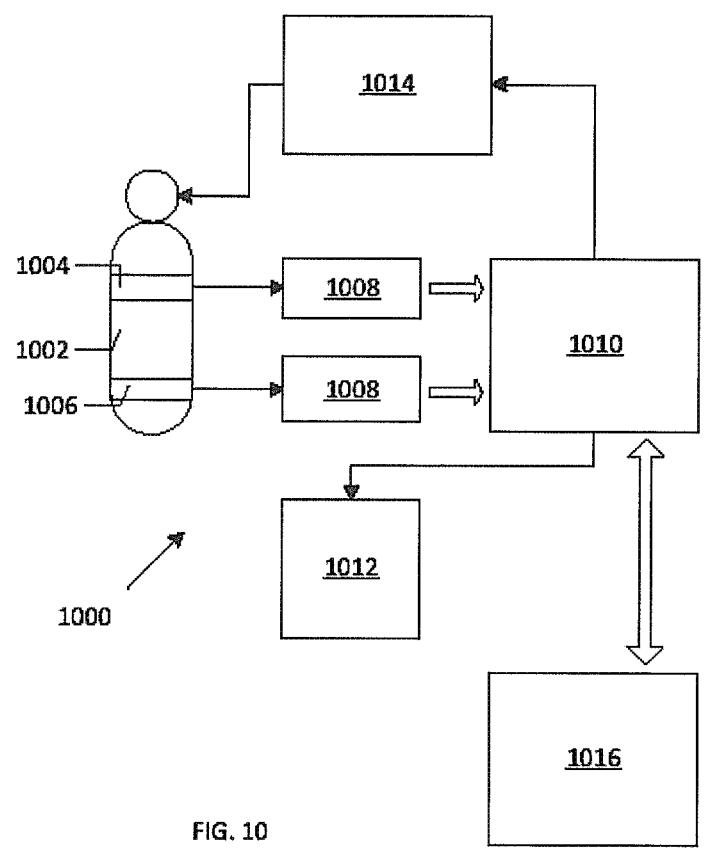
FIG. 10 is a block diagram of the overall apparatus.

Referring now also to FIG. 10, one embodiment of a system indicated generally by the reference numeral 1000 may implement the feedback loop illustrated in FIG. 9. A patient indicated generally by the reference numeral 1002 is fitted with a pair of inductive bands 1004 on the ribcage and 1006 on the abdomen, which are monitored by sensor modules 1008. As discussed above, there may be a single sensor module 1008 monitoring both bands 1004, 1006, in which case the sensor module may determine the phase (φ) between the two bands. Alternatively, there may be a separate sensor module 1008 for each band, in which case the sensor module is preferably directly mounted on the band, so that there is no associated wiring on the patient 1002. The sensor modules 1008 transmit their data wirelessly to a processing unit 1010, which maybe a tablet computer such as an As previously noted, utilizing the present method (iPad® tablet/firmware device) for assessing work of breathing indices, it is now possible to close the treatment loop. Thus, a clinical operator can increase or decrease end distending pressure or the entire system can be closed-loop such that the iPad iPad® tablet, firmware, or other controlling processor can directly control a CPAP, PEEP, HFNC flow, or other breathing assist device, depending on the degree of disability. Furthermore, this diagnostic device concept can be combined with other forms of respiratory support (conventional mechanical ventilators with PEEP, as well as high frequency ventilators (HFV) with bias flow for increasing end distending pressure) to treat respiratory insufficiency (respiratory muscle fatigue). As discussed above, the sensor module or modules 1008 usefully digitize and perform some pre-processing of the output from the inductive bands, in order to reduce the volume of data transmitted. That both saves on wireless bandwidth and reduces the power consumption of the transmitting modules 1008. The processing unit 1010 receives and processes the data from the sensor module or modules 1008. The processing unit 1010 may compute the breathing parameters, compute the respiratory fatigue index (RFI), calculate the error between the actual and desired RFIs, and display any or all of those results on a screen 1012.

In dependence on the error between the actual state of the patient as derived from the inductive bands 104, 106 and a desired state, whether obtained through an error in RFI or otherwise, the processing unit 1010 outputs as appropriate a command to a respiratory therapy device 1014, which may be, for example, a CPAP machine, to apply, increase, maintain, or decrease a respiratory therapy administered to the patient 1002.

Once the closed loop illustrated in FIGS. 9 and 10 is established, it may in many cases be left to operate for substantial periods with only minimal supervision from medical personnel. However, medical personnel may monitor the state of the system by direct examination of the patient and/or by using information on the display 1012, and may intervene by inputting commands and/or changing preset or previously entered parameters through a user interface (not shown in detail) of the processing device 1010.

A communication link may also be provided between the processing device 1010 and a remote location 1016, such as a nurse's station, if the apparatus is being used in a hospital or similar setting, or a doctor's office. The remote communication link enables a person at the remote location to monitor the state of the patient and the apparatus, and may also enable the doctor to authorize or make adjustments to the apparatus settings remotely. Remote communication would be particularly useful when the system 1000 is used for home care, so that the caregiver at the location 1016 can remotely make changes to the therapy based on the information that they are receiving. The communication may use any convenient channel, depending on the circumstances, including wired or wireless internet or WIFI transmission.

The presented noninvasive method and instrumentation provides insight into the diagnosis of numerous respiratory disorders and enables differentiation, in many cases, between restrictive and obstructive disorders. As described herein, it will be possible to demonstrate normal PF, as well as increased WOB indices with respiratory disorders in real-time and at point-of-care. In addition, the respiratory fatigue index (RFI), tidal flow-volume relationships and variance in phase angle patterns will be useful in treatment protocols to guide respiratory therapy by directly controlling the respiratory support devices via the measured and calculated parameters and appropriately adjusting an individual support device (e.g., CPAP) to return the patient to within normal limits. As previously noted, in an open-loop system configuration, the clinical caregiver can take the information from the display shown in FIG. 4 and adjust the respiratory support device.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed. The various embodiments and elements can be interchanged or combined in any suitable manner as necessary.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

The invention claimed is:

1. A method of managing respiration of a subject suffering from non-sleep apnea pulmonary dysfunctions including respiratory distress syndrome (RDS), bronchopulmonary dysplasia (BPD), and respiratory muscle dysfunction for subjects with neuromuscular diseases by detecting a decrease in lung compliance and/or an increase in pulmonary resistance, comprising the steps of:
placing a first respiratory motion monitor around a ribcage of the subject;
placing a second respiratory motion monitor around an abdomen of the subject;
monitoring respiratory motion of the ribcage of the subject using the first respiratory motion monitor;
monitoring respiratory motion of the abdomen of the subject using the second respiratory motion monitor;
receiving in a processor ribcage motion data from the first respiratory motion monitor indicative of the motion of the ribcage and receiving abdomen motion data from the second respiratory motion monitor indicative of the motion of the abdomen;
deriving in the processor, using the ribcage motion data and the abdomen motion data, a numerical value indicative of a quality of respiration, wherein the numerical value is a respiratory fatigue index (RFI) calculated according to the following formula:

$$RFI = \alpha_1(\Phi) + \alpha_2(LBI) + \alpha_3(RR) + \alpha_4(HR) + \alpha_5(\sigma) \quad \text{(Formula 1)}$$

where parameters include::
$\alpha_1$, $\alpha_2$, $\alpha_3$, $\alpha_4$, and $\alpha_5$ are weighting coefficients, Φ is a phase angle calculated between the ribcage motion data and the abdomen motion data, LBI is a labored breathing index calculated based on changes in a measured volume of the rib cage from the ribcage motion data, RR is a respiratory rate as measured from the ribcage motion data and the abdomen motion data, HR is a variance of a detected heart rate from a predetermined heart rate, and σ is a variance of the phase angle from a predetermined phase angle:

when the numerical value is within a first threshold of a first state, not applying respiratory therapy;

when the numerical value is outside the first threshold by less than a first margin, applying the respiratory therapy at a first intensity; and when the numerical value is outside the first threshold by more than the first margin, applying the respiratory therapy at a second intensity greater than the first intensity.

2. The method of claim 1, further comprising the steps of:
while applying the respiratory therapy to the subject,
monitoring respiratory motion of the ribcage of the subject using the first respiratory motion monitor;
monitoring respiratory motion of the abdomen of the subject using the second respiratory motion monitor; and
receiving updated ribcage motion data and abdomen motion data;
deriving from the updated ribcage motion data and abdomen motion data a renewed numerical value based on an updated respiratory fatigue index (RFI) calculated according to Formula 1;
when the renewed numerical value is outside the first threshold, increasing the previously applied intensity of the respiratory therapy; and
when the renewed numerical value is outside a second threshold, reducing the previously applied intensity of the respiratory therapy.

3. The method of claim 1, wherein the respiratory therapy is selected from continuous positive airway pressure (CPAP), positive end-expiratory pressure (PEEP), high flow nasal cannulae flow (HFNC), and bias flow with high frequency ventilation (HFV).

4. The method of claim 1, wherein the first and second respiratory motion monitors are respiratory inductance plethysmography (RIP) devices.

5. The method of claim 1, further comprising initially setting the weighting coefficients $\alpha_1=\alpha_2=\alpha_3=\alpha_4=\alpha_5$.

6. The method of claim 5, further comprising the step of, after determining the parameters, adjusting one or more of the coefficients α in a direction to reduce the relative weighting of one or more parameters having a high value relative to one or more parameters having a lower value.

7. The method of claim 1, further comprising the step of monitoring the respiration for a period of at least five minutes, deriving multiple numerical values during the period and averaging the multiple numerical values.

8. The method of claim 1, wherein the phase angle is calculated by normalizing the ribcage motion data (y) and the abdomen motion data (x) based on a plurality (N) of received signals of ribcage motion data and abdomen motion data using the following formula:

$$\varphi = \cos^{-1}[\Sigma x(n)y(n)]/(\{\sqrt{\Sigma x(n)^2 \Sigma y(n)^2}\}) \quad \text{(Formula 3)}$$

where: n=0 to N−1.

9. An apparatus for managing respiration of a subject suffering from non-sleep apnea pulmonary dysfunctions including respiratory distress syndrome (RDS), bronchopulmonary dysplasis (BPD), and respiratory muscle dysfunction for subjects with neuromuscular diseases by detecting a decrease in lung compliance and/or an increase in pulmonary resistance comprising:

a first respiratory motion monitor that, in operation, is associated with a ribcage of the subject and configured to detect motion of the subject's ribcage and provide ribcage motion data indicative of the detected motion;

a second respiratory motion monitor that, in operation, is associated with an abdomen of the subject and configured to detect motion of the subject's abdomen and provide abdomen motion data indicative of the detected motion;

a central processor that is operative to derive from the ribcage motion data and the abdomen motion data a numerical value indicative of a quality of respiration, the numerical value is a respiratory fatigue index (RFI) calculated according to the following formula:

$$RFI = \alpha_1(\Phi) + \alpha_2(LBI) + \alpha_3(RR) + \alpha_4(HR) + \alpha_5(\sigma) \quad \text{(Formula 2)}$$

where parameters include:
$\alpha_1, \alpha_2, \alpha_3, \alpha_4$, and $\alpha_5$ are weighting coefficients,
Φ is a phase angle calculated between the ribcage motion data and the abdomen motion data,
LBI is a labored breathing index calculated based on changes in a measured volume of the rib cage from the ribcage motion data,
RR is a respiratory rate as measured from the ribcage motion data and the abdomen motion data,
HR is a variance of a detected heart rate from a predetermined heart rate, and
σ is a variance of the phase angle from a predetermined phase angle; and a respiratory therapy device responsive to an output from the processor to:
when the numerical value is within a first threshold of a first state, not apply respiratory therapy;
when the numerical value is outside the first threshold by less than a first margin, apply the respiratory therapy at a first intensity; and
when the numerical value is outside the first threshold by more than the first margin, apply the respiratory therapy at a second intensity greater than the first intensity.

10. The apparatus of claim 9, wherein each of said respiratory motion monitors comprises a sensor that, in use, is attached to the patient, a processor connected to the sensor that obtains an output from the sensor, a wireless transmitter that transmits, in real time, the sensor output, as refined by the processor, as the ribcage motion data or abdomen motion data, as applicable, to the central processor, and a battery power supply.

11. The apparatus of claim 9, further operative to:
while applying the respiratory therapy to the subject,
monitor an additional respiratory motion of the ribcage of the subject and provide updated ribcage motion data;
monitor an additional respiratory motion of the abdomen of the subject and provide updated abdomen motion data; and
derive from the updated ribcage motion data and updated abdomen motion data a renewed numerical value based on an updated respiratory fatigue index (RFI) calculated according to Formula 2;

when the renewed numerical value is outside the first threshold, increase the previously applied intensity of the respiratory therapy; and when the renewed numerical value is outside a second threshold, reduce the previously applied intensity of the respiratory therapy.

12. The apparatus of claim 9, wherein the respiratory therapy device is selected from a group consisting of devices operative to administer continuous positive airway pressure (CPAP), positive end-expiratory pressure (PEEP), high flow nasal cannulae flow (HFNC), and bias flow with high frequency ventilation (HFV).

13. The apparatus of claim 9, wherein the monitors comprise respiratory inductance plethysmography (RIP) monitors.

14. The apparatus of claim 9, wherein the weighting coefficients are initially set so that $\alpha_1 = \alpha_2 = \alpha_3 = \alpha_4 = \alpha_5$.

15. The apparatus of claim 14, further operative, after determining the parameters, to adjust one or more of the coefficients $\alpha$ in a direction to reduce the relative weighting of one or more parameters having a high value relative to one or more parameters having a lower value.

16. The apparatus of claim 9, further operative to monitoring the respiration for a period of at least five minutes, deriving multiple numerical values during the period and averaging the multiple numerical values.

17. The apparatus of claim 9, wherein the phase angle is calculated by normalizing the ribcage motion data (y) and the abdomen motion data (x) based on a plurality (N) of received signals of the ribcage motion data and the abdomen motion data using the following formula:

$$\phi = \cos^{-1}[\Sigma x(n)y(n)]/(\{\sqrt{\phantom{-}}[\Sigma x(n)^2 \Sigma y(n)^2]\}) \quad \text{(Formula 4)}$$

where: n=0 to N−1.

* * * * *

UNITED STATES PATENT AND TRADEMARK OFFICE
CERTIFICATE OF CORRECTION

PATENT NO. : 11,234,640 B2
APPLICATION NO. : 16/020582
DATED : February 1, 2022
INVENTOR(S) : Tariq Rahman et al.

It is certified that error appears in the above-identified patent and that said Letters Patent is hereby corrected as shown below:

In the Claims

In Column 12, Claim 1, Line 42:
Replace "dysplasis" with "dysplasia"

In Column 14, Claim 9, Line 4:
Replace "dysplasis" with "dysplasia"

Signed and Sealed this
Nineteenth Day of April, 2022

*Katherine Kelly Vidal*
Katherine Kelly Vidal
*Director of the United States Patent and Trademark Office*